United States Patent
Dickinson et al.

(10) Patent No.: US 6,398,197 B1
(45) Date of Patent: Jun. 4, 2002

(54) WATER CHAMBER

(75) Inventors: Philip John Dickinson; David Wixey, both of Auckland (NZ)

(73) Assignee: Fisher & Paykel Limited, Auckland (NZ)

( * ) Notice: Subject to any disclaimer, the term of this patent is extended or adjusted under 35 U.S.C. 154(b) by 0 days.

(21) Appl. No.: 09/564,508

(22) Filed: May 4, 2000

(30) Foreign Application Priority Data

May 10, 1999 (NZ) .................................................. 335694

(51) Int. Cl.[7] .................................................. B01F 3/04
(52) U.S. Cl. ........................ 261/141; 261/30; 261/72.1; 261/119.1; 261/DIG. 65
(58) Field of Search ........................ 261/30, 72.1, 141, 261/142, 119.1, DIG. 65; 96/367, 370

(56) References Cited

U.S. PATENT DOCUMENTS

| | | | | |
|---|---|---|---|---|
| 485,127 A | * | 10/1892 | Lynch | 261/30 |
| 933,301 A | * | 9/1909 | Hartmann | 261/30 |
| 1,059,622 A | * | 4/1913 | Long et al. | 261/30 |
| 1,777,510 A | * | 10/1930 | Voigt | 261/119.1 |
| 1,813,959 A | * | 7/1931 | Romanoff | 261/119.1 |
| 2,710,178 A | * | 6/1955 | Froelich | 261/119.1 |
| 4,152,379 A | * | 5/1979 | Suhr | 261/DIG. 65 |
| 4,487,746 A | * | 12/1984 | Tahiliani | 261/119.1 |
| 5,209,225 A | * | 5/1993 | Glenn | 261/DIG. 65 |
| 5,762,663 A | * | 6/1998 | Asada | 261/119.1 |

* cited by examiner

Primary Examiner—C. Scott Bushey
(74) Attorney, Agent, or Firm—Trexler, Bushnell, Giangiorgi, Blackstone & Marr, Ltd.

(57) ABSTRACT

A water chamber has a horizontally orientated gas inlet with an elongate flow tube extending into the water chamber from the inner periphery of the gases inlet. An inlet end of the elongate flow tube covers the inlet and an outlet end of the flow tube is spaced from the wall of the chamber. In use the flow tube receives gases supplied to the gases inlet, the gases pass through the flow tube and exit the flow tube at the outlet end distant from the wall.

20 Claims, 3 Drawing Sheets

WATER CHAMBER

BACKGROUND TO THE INVENTION i) Field of the Invention

The present invention relates to water chambers for gases humidification and in particular to water chambers for "slide-on" humidifiers and CPAP machines.

ii) Summary of the Prior Art

In the prior art humidification systems are well known which include a heater base and a disposable humidifier chamber which is fitted onto the heater base and within which a supply of water can be heated by the heater base. Air passing through the chamber from an inlet to an outlet is humidified by the evaporation of water from the water supply.

Humidifier chambers of this type are also now used in compact and portable ventilation machines, for example machines intended for the home treatment of obstructive sleep apnoea (CPAP machines). These machines pose a particular difficulty as the air flow is delivered directly to the humidifier chamber from the air blower of the CPAP machine and this can generate an annoying noise level within the humidifier chamber. Furthermore where the CPAP machine is adapted for use with slide-on humidifier chambers, and the connection of the chamber to the machine is accomplished within the single sliding movement, the inlet air port is consequently provided horizontally through a side of the chamber. Locating the inlet port in the side of the chamber significantly increases the likelihood of water spillage from the chamber if the chamber is tilted with water therein. This can be of particular disadvantage where the water may flow out through the inlet port and into the air blower of the CPAP machine.

SUMMARY OF THE INVENTION

It is therefore an object of the present invention to provide a water chamber which at least goes some way towards overcoming the above disadvantages or which will at least provide the public with a useful choice.

In a first aspect the invention consists in a water chamber adapted for use in conjunction with a heater base and having a horizontally oriented gases inlet in a wall thereof the improvement comprising an elongate flow tube extending into said water chamber from the inner periphery of said gases inlet, an inlet end of said elongate flow tube covering said inlet and an outlet end of said flow tube being spaced from the wall of said chamber, said flow tube in use receiving, at said inlet end, gases supplied to said gases inlet, said gases passing through said flow tube and exiting said flow tube at said outlet end distant from said wall.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION

Figure 1:
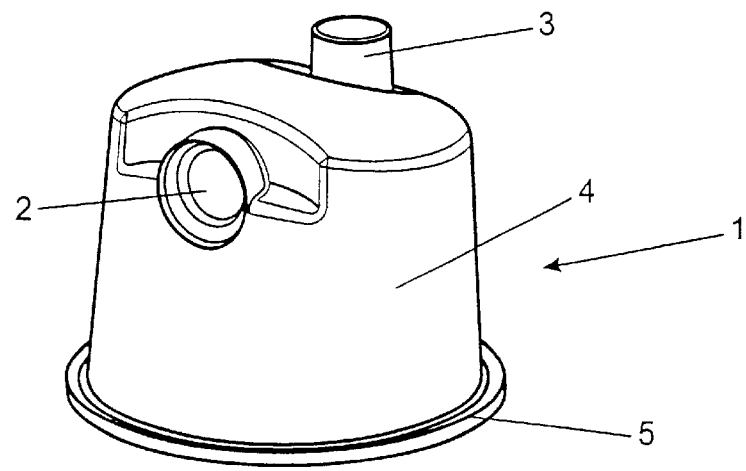
FIG. 1 is a perspective view of a water chamber according to the preferred embodiment of the present invention.
Figure 2:
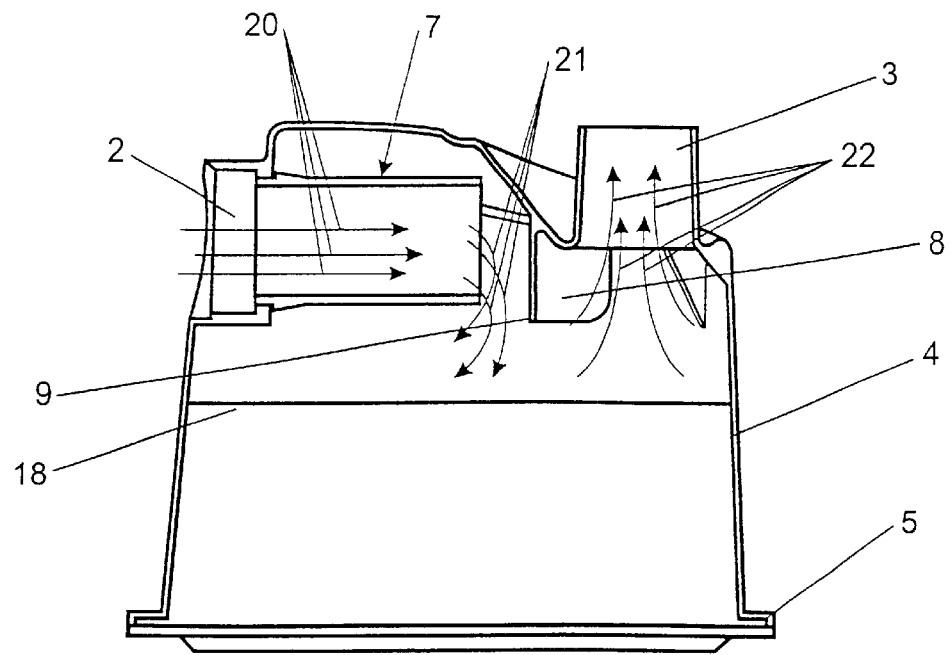
FIG. 2 is a cross sectional side elevation of the chamber of FIG. 1.

Referring to FIGS. 1 and 2 a water chamber is illustrated particularly for use in a portable CPAP machine adapted to receive slide-on chambers and which makes the gases inlet connection to the chamber in the same slide-on motion. The chamber 1 has a transparent plastic shell 4 and a heat conductive base 6. The shell 1 and heat conductive base 6 are connected at a peripheral flange 5 which also serves as a securing flange in the slide-on connection with the CPAP machine. The chamber includes a horizontally aligned gases inlet 2 which in use fits over a blower nozzle of the CPAP machine. A gases outlet 3 is provided in the roof of the chamber 1. The gases outlet 3 may be adapted to take standard breathing circuit fittings.

Referring to FIG. 2 the water chamber 1 is shown in cross section. In the present invention the water chamber 1 includes an inlet extension tube 7 extending inwardly into the chamber interior from the periphery of the gases inlet 2. In the most preferred embodiment the chamber further includes a curved downwardly extending baffle 8 located between the gases outlet 3 and the termination of the inlet extension tube 7 to ensure against gases short circuiting the chamber by flowing directly from the extension 7 to the outlet 3. With the baffle 8 in place the gases are forced to follow a more tortuous path ensuring adequate humidification during their journey through the chamber 1.

The lower edge 9 of the baffle 8 preferably extends lower than the lower edge of the inlet extension tube 7.

A narrow rib 18 may be provided on the inside wall of the clear plastic shell 4 which will show visually from the outside of the shell to act as an optimum water level "fill" marker.

In use air is received from the blower of the CPAP machine, or if the chamber is used in a standard humidification circuit, then from the ventilator, through inlet 2. Travelling through the inlet extension tube 7 the air is imparted with a more controlled laminar flow than is generally provided by the blower, as indicated by arrows 20. On exiting the inlet extension tube 7 the air is deflected by the baffle 8 to the various environs of the water chamber as indicated by arrows 21. Air eventually leaves the chamber through outlet 3 as indicated by arrows 22.

Figure 6:
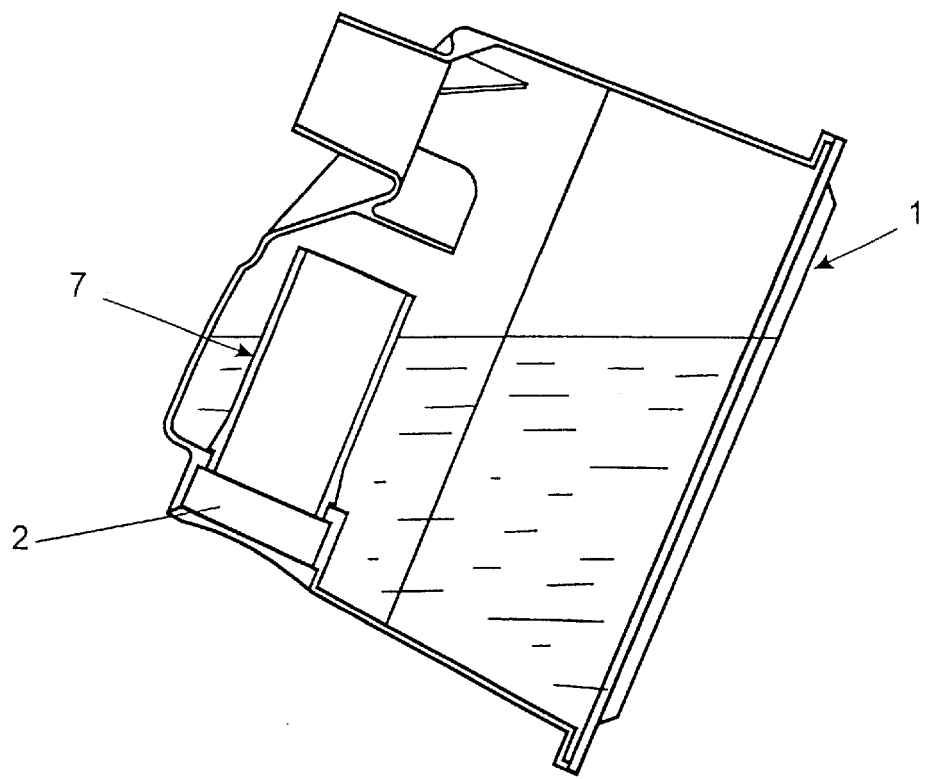
FIG. 6 is a cross sectional side elevation of the chamber of FIG. 1 in use with water therein and in a tilted condition demonstrating the operation of the inlet extension tube 7 in reducing the capacity for leakage through the gases inlet 2.

By providing the inlet extension tube 7 and therefore imparting an improved flow pattern to the inlet flow, it has been found that the noise level of the humidifier chamber has been significantly reduced, and, in conjunction with the curved baffle 8, effective operation of the water chamber 1 has been maintained. Additionally, with reference to FIG. 6, the inlet extension tube 7 acts as a weir against water flow back through gases inlet 2 upon tilting of the chamber 1.

These benefits have been achieved while maintaining, in the design shown, S equivalent external appearance and size, and the same ease of use and simplicity to the user, as earlier chambers.

Figure 3:
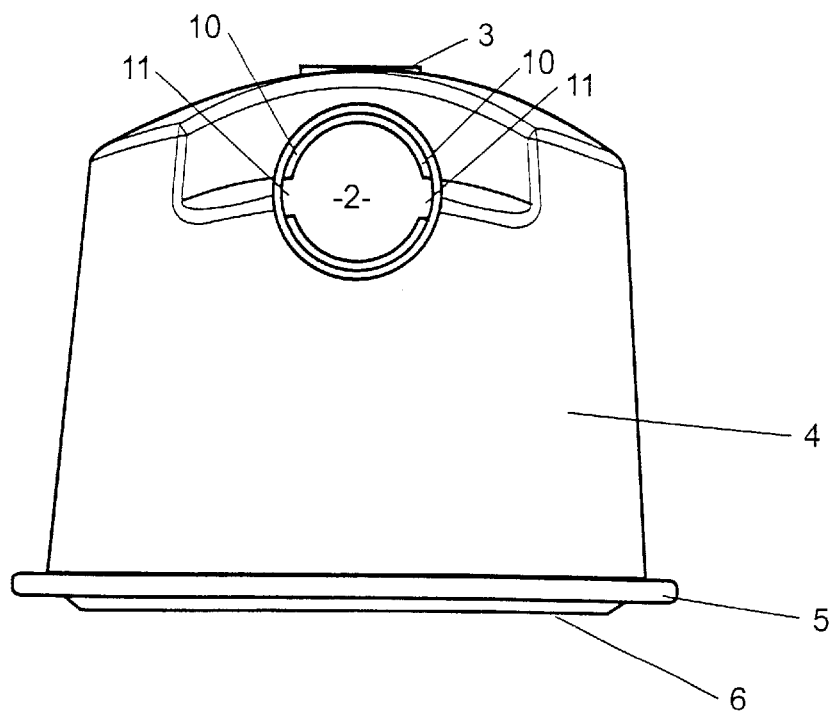
FIG. 3 is a front elevation of the chamber of FIG. 2 before insertion of the inlet extension tube.
Figure 4:
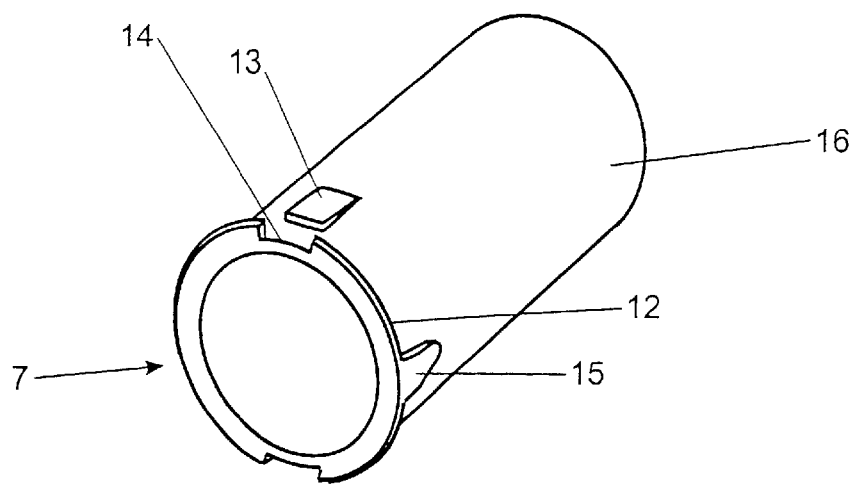
FIG. 4 is a perspective view of an extension tube according to the preferred embodiment of the present invention.
Figure 5:
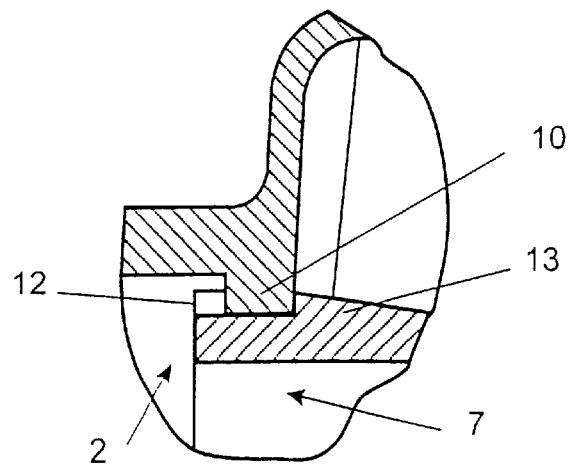
FIG. 5 is a cross sectional side elevation detail of engagement of the extension tube of FIG. 4 with the sealing flange of the chamber inlet.

Referring now to FIGS. 3–5, these depict the preferred embodiment of the present invention, and in particular the detail of the connection between the inlet extension tube 7 and the plastic shell 1. Note that the inlet extension tube 7 is preferably moulded from the same clear thermoplastic material as the chamber shell 4.

For ease of assembly the extension tube 7 is preferably provided as a snap fit to the inlet 2, so that it can be pushed into the chamber through the inlet 2 and, upon application of sufficient force, snap into a substantially watertight and secure condition.

To these ends the inlet 2 is provided with an inwardly perpendicularly extending annular flange 10 at the inner end thereof The inlet extension tube 7 includes a similar perpendicularly outwardly extending flange 12 from one end of the generally tapering tubular body 16. The flanges 10 and 12 act together as sealing flanges in the fitted and assembled condition as shown in FIGS. 2 and 5.

To retain the extension tube 7 in the assembled condition, against both translational and rotational movement several securing mechanisms are provided In each case the securing mechanism may be provided on either of the inlet 2 or the inlet extension tube 7, however it is preferred that they be on the inlet extension tube 7, as both components are intended for injection moulding and injection moulding of certain protrusions on the inner surface of the inlet 2 would be considerably more difficult than on the outer surface of the tube 7.

To secure the tube 7 against translational movement, and in a sealing condition between the sealing flanges 10, 12 a plurality (preferably two) of remaining clip protrusions 13 are provided spaced around the circumference of the tubular body 16 of the extension tube 7 adjacent but spaced from the flange 12. The protrusions 13 are preferably spaced from the flange 12 at a distance correlating to the thickness of flange 10. In use, as depicted in the detail FIG. 5 the flange 10 is secured between an upstanding edge of the protrusion 13 and the leading face of the flange 12.

Particularly for case of manufacture, and ensuring a simple two part injection mould, a notch 14 is allowed in the flange 12 of the tubular extension 7 adjacent the protrusion 13.

To retain the tubular extension 7 against rotational movement when snap fitted into location one or more, preferably 2, locating protrusions 15 are provided circumferentially distrbuted on the outer surface of the tubular body 16 of the inlet extension tube 7, adjacent and contiguous with the outwardly and perpendicularly extending flange 12. The locating protrusions 15 are preferably generally tapered in both the circumferential and axial direction. Complementary notches 11 are provided in the inwardly extending flange 10 of the inlet 2. In fitting the inlet extension tube 7 the protrusions 15 are aligned with the notches 11, and upon fill insertion of the tube 7 the protrusions 15 enter into a tight frictional fit with the notches 11 ensuring substantial if not complete sealing. Given their particular configuration the protrusions 15 could be readily provided on the inner surface of the inlet 2 in which case complementary notches would instead be provided on the flange 12 of the inlet extension tube 7.

It will be readily appreciated that the construction as described is simple to manufacture and each of the plastic components is itself capable of simple injection moulding. Consequently a water chamber according to the present invention is, while providing significant advantages, not significantly more expensive than existing chambers.

What is claimed is:

1. In a water chamber adapted for use in conjunction with a heater base and having a horizontally oriented gases inlet in a wall thereof the improvement comprising an elongate flow tube extending into said water chamber from the inner periphery of said gases inlet, an inlet end of said elongate flow tube covering said inlet and an outlet end of said flow tube being spaced from the wall of said chamber, said flow tube in use receiving, at said inlet end, gases supplied to said gases inlet, said gases passing through said flow tube and exiting said flow tube at said outlet end distant from said wall.

2. A water chamber as claimed in claim 1 wherein said flow tube extends for a distance of at least a quarter of the diameter of said water chamber.

3. A water chamber as claimed in claim 2 wherein said gases inlet and said flow tube are aligned radially and said flow tube extends to approximately the middle of said chamber.

4. A water chamber as claimed in claim 1 wherein said chamber includes a vertically oriented gases outlet in the roof of said chamber, said gases outlet located beyond the termination of said flow tube, and a baffle wall extending downwardly from the roof of said chamber between the outlet end of said flow tube and said gases outlet.

5. A water chamber as claimed in claim 4 wherein said baffle wall is curved to be closest to said flow tube at the centre thereof, the ends of said baffle wall curved away from said flow tube.

6. A water chamber as claimed in claim 1 wherein said water chamber comprises a transparent plastic shell open at the bottom and having a peripheral flange, a heat conductive plate enclosing said bottom of said shell and sealed at its periphery to said flange, and said elongate flow tube comprises a tubular extension tube member fitted at said gases inlet.

7. A water chamber as claimed in claim 6 wherein said extension tube includes a perpendicularly extending sealing flange at one end thereof, and said gases inlet of said water chamber includes a perpendicularly and inwardly extending annular, sealing flange, and said sealing flange of said extension tube and said sealing flange of said water chamber inlet abut one another in an assembled condition.

8. A water chamber as claimed in claim 7 wherein either said extension tube or said gases inlet includes a plurality of retaining protrusions spaced around the circumference thereof, adjacent but spaced from the respective said sealing flange such that in an assembled condition said protrusions and the said adjacent sealing flange engage the other said sealing flange therebetween.

9. A water chamber as claimed in claim 8 wherein said adjacent sealing flange includes a notch in the vicinity of each said retaining protrusion.

10. A water chamber as claimed in claim 7 wherein either said extension tube or said gases inlet to said water chamber includes one or more locating protrusions around the circumference thereof adjacent to and contiguous with their respective sealing flange, and the other said sealing flange includes one or more corresponding notches into which said retaining protrusions engage to restrain said extension tube against rotational movement.

11. A water chamber as claimed in claims 3 wherein said chamber includes a vertically oriented gases outlet in the roof of said chamber, said gases outlet located beyond the termination of said flow tube, and a baffle wall extending downwardly from the roof of said chamber between the outlet end of said flow tube and said gases outlet.

12. A water chamber as claimed in claim 11 wherein said baffle wall is curved to be closest to said flow tube at the centre thereof, the ends of said baffle wall curved away from said flow tube.

13. A water chamber as claimed in claim 3 wherein said water chamber comprises a transparent plastic shell open at the bottom and having a peripheral flange, a heat conductive plate enclosing said bottom of said shell and sealed at its periphery to said flange, and said elongate flow tube comprises a tubular extension tube member fitted at said gases inlet.

14. A water chamber as claimed in claim 13 wherein said extension tube includes a perpendicularly extending sealing flange at one end thereof, and said gases inlet of said water chamber includes a perpendicularly and inwardly extending annular sealing flange, and said sealing flange of said extension tube and said sealing flange of said water chamber inlet abut one another in an assembled condition.

15. A water chamber as claimed in claim 4 wherein said water chamber comprises a transparent plastic shell open at the bottom and having a peripheral flange, a heat conductive plate enclosing said bottom of said shell and sealed at its periphery to said flange, and said elongate flow tube comprises a tubular extension tube member fitted at said gases inlet.

16. A water chamber as claimed in claim 15 wherein said extension tube includes a perpendicularly extending sealing flange at one end thereof, and said gases inlet of said water chamber includes a perpendicularly and inwardly extending annular sealing flange, and said sealing flange of said extension tube and said sealing flange of said water chamber inlet abut one another in an assembled condition.

17. A water chamber as claimed in claim 16 wherein either said extension tube or said gases inlet includes a plurality of retaining protrusions spaced around the circumference thereof, adjacent but spaced from the respective said sealing flange such that in an assembled condition said protrusions and the said adjacent sealing flange engage the other said sealing flange therebetween.

18. A water chamber as claimed in claim 15 wherein either said extension tube or said gases inlet to said water chamber includes one or more locating protrusions around the circumference thereof adjacent to and contiguous with their respective sealing flange, and the other said sealing flange includes one or more corresponding notches into which said retaining protrusions engage to restrain said extension tube against rotational movement.

19. A water chamber as claimed in claim 7 wherein either said extension tube or said gases inlet to said water chamber includes one or more locating protrusions around the circumference thereof adjacent to and contiguous with their respective sealing flange, and the other said sealing flange includes one or more corresponding notches into which said retaining protrusions engage to restrain said extension tube against rotational movement.

20. A water chamber as claimed in claim 8 wherein either said extension tube or said gases inlet to said water chamber includes one or more locating protrusions around the circumference thereof adjacent to and contiguous with their respective sealing flange, and the other said sealing flange includes one or more corresponding notches into which said retaining protrusions engage to restrain said extension tube against rotational movement.

* * * * *